(12) United States Patent
Pain et al.

(10) Patent No.: US 10,568,729 B2
(45) Date of Patent: Feb. 25, 2020

(54) DEVICE FOR TRANSCATHETER INSERTION INTO THE AORTIC ROOT AT THE SINOTUBULAR JUNCTION

(71) Applicants: Centre Hospitalier Universitaire de Saint-Etienne, Saint-Etienne (FR); Aorticlab Sàrl, Savigny (CH)

(72) Inventors: Bernard Pain, Monistrol-sur-Loire (FR); Marco Vola, Saint-Priest-en-Jarez (FR); Enrico Pasquino, Marentino (IT)

(73) Assignees: AorticLab Italy srl, Colleretto, Giacosa, TO (IT); Centre Hospitalier Universitaire de Saint-Étienne, Saint-Étienne (FR)

( * ) Notice: Subject to any disclaimer, the term of this patent is extended or adjusted under 35 U.S.C. 154(b) by 142 days.

(21) Appl. No.: 15/315,731

(22) PCT Filed: Jun. 4, 2015

(86) PCT No.: PCT/FR2015/051488
§ 371 (c)(1),
(2) Date: Dec. 2, 2016

(87) PCT Pub. No.: WO2015/185870
PCT Pub. Date: Dec. 10, 2015

(65) Prior Publication Data
US 2017/0119517 A1    May 4, 2017

(30) Foreign Application Priority Data
Jun. 5, 2014   (FR) ...................................... 14 55144

(51) Int. Cl.
*A61F 2/01*    (2006.01)
*A61F 2/24*    (2006.01)

(52) U.S. Cl.
CPC ............ *A61F 2/013* (2013.01); *A61F 2/2412* (2013.01)

(58) Field of Classification Search
CPC .. A61F 2/013; A61F 2/2412; A61F 2002/011; A61F 2002/015; A61F 2002/016
See application file for complete search history.

(56) References Cited

U.S. PATENT DOCUMENTS

| 6,692,513 B2 * | 2/2004 | Streeter ..................... A61F 2/01 606/200 |
| 2005/0010285 A1 * | 1/2005 | Lambrecht ............ A61F 2/2427 623/2.18 |

(Continued)

FOREIGN PATENT DOCUMENTS

WO   WO 02/47539   6/2002
WO   PCT/US2003/036639   11/2003

(Continued)

OTHER PUBLICATIONS

International Search Report of the parent application PCT/FR2015/051488 dated Aug. 7, 2015.

(Continued)

*Primary Examiner* — Tuan V Nguyen
(74) *Attorney, Agent, or Firm* — Andre Roland S.A.; Nikolaus Schibli

(57) ABSTRACT

A device for transcatheter insertion into the aortic root at the sinotubular junction by a wire guide and a catheter for protecting surrounding tissues, the device including an assembly serving as a valvular embolic filter, configured to slide in a guided manner inside the catheter, the assembly configured to form, in the aortic root of an aorta, a safety enclosure ensuring a valve function and a protective function against embolic accidents, wherein the assembly includes, a tubular body, and a filtration and valve part configured to deploy outside the catheter or retract inside the (Continued)

Figure 3:
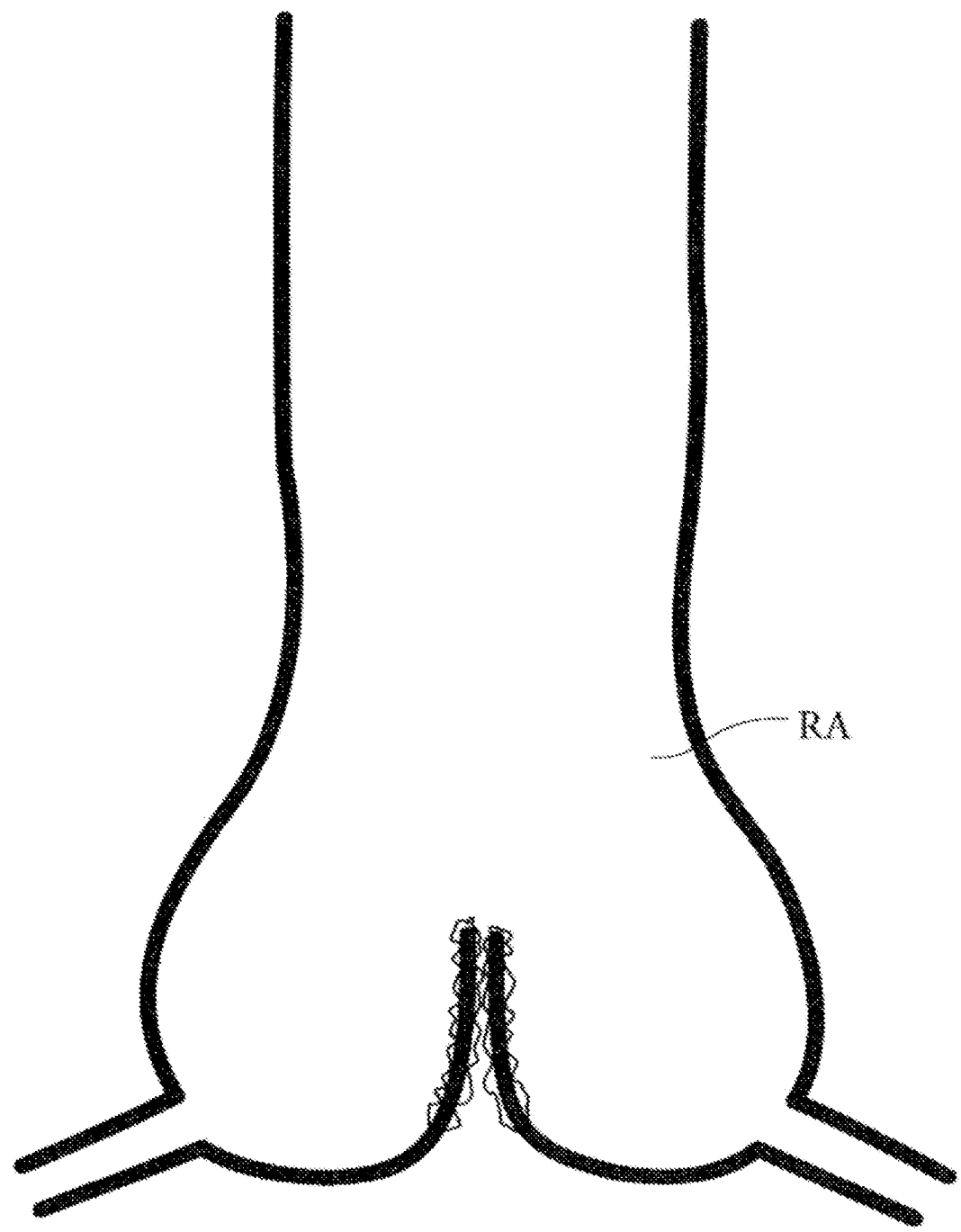

catheter, wherein the tubular body is secured, at one end, to the filtration and valve part, wherein the filtration and valve part forms the valvular embolic filter and a temporary valve, wherein the filtration and valve part is configured to prevent regurgitation of blood when deployed outside the catheter for covering a native aortic valve with a seat secured in the aortic root at sinuses of valsalva without obstructing a blood flow.

12 Claims, 19 Drawing Sheets

(56) References Cited

U.S. PATENT DOCUMENTS

2013/0253571 A1* 9/2013 Bates .................. A61F 2/013
 606/200
2013/0325117 A1* 12/2013 Bruchman ............. A61L 27/48
 623/2.17
2013/0331929 A1* 12/2013 Mitra ................... A61L 31/145
 623/2.11

FOREIGN PATENT DOCUMENTS

WO WO 2004/043293 5/2004
WO 2006-507862 A1 3/2006

OTHER PUBLICATIONS

Written Opinion of the International Search Authority of the parent application PCT/FR2015/051488 dated Aug. 7, 2015, and English translation thereof.
Office Action from the Japanese Patent Office for JP2017-516213 dated May 7, 2019 and English translation thereof.

* cited by examiner

Fig. 1
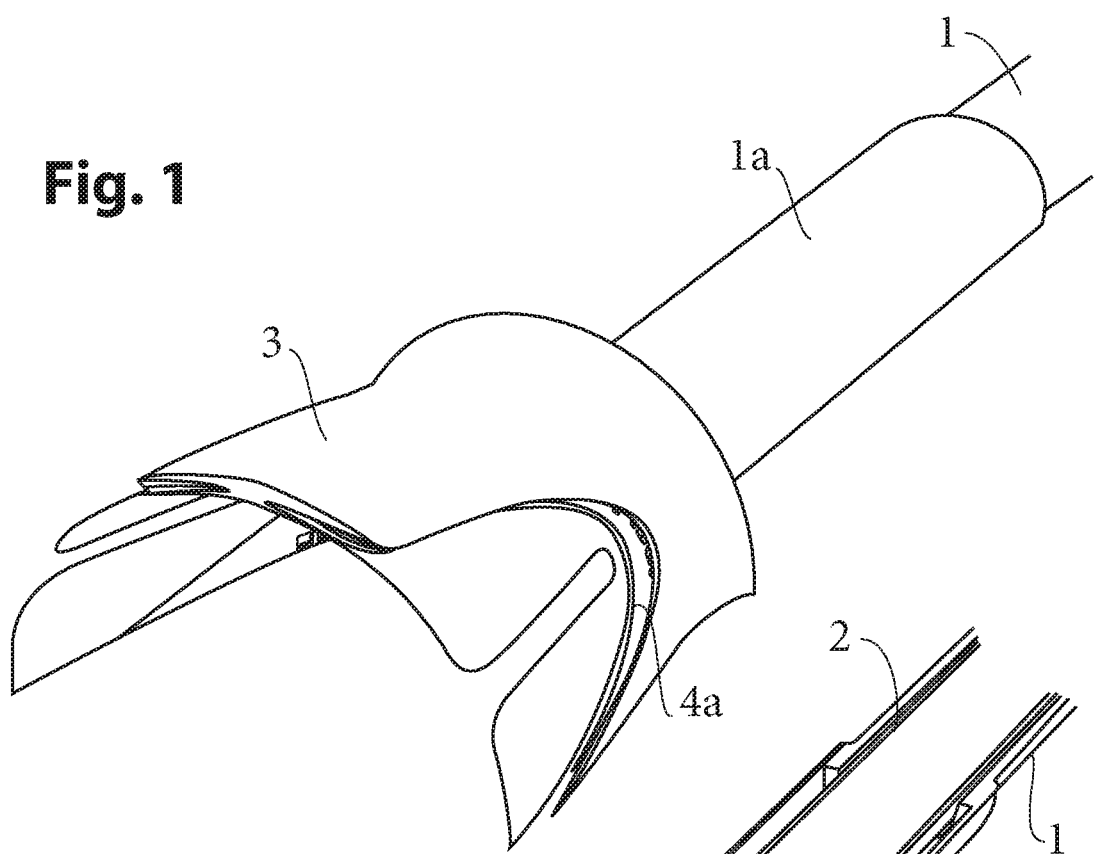
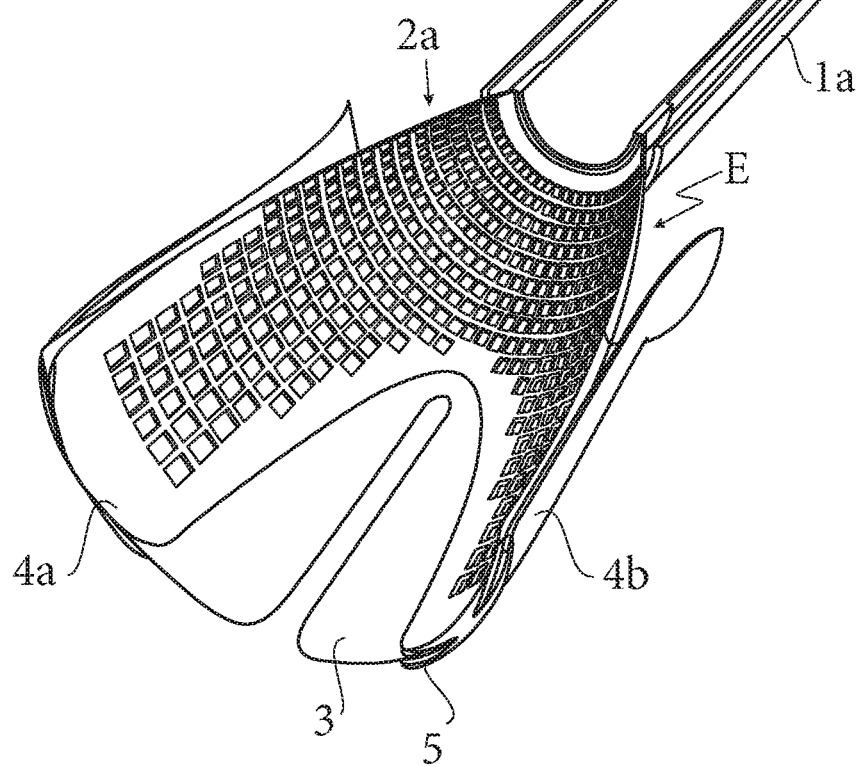
Fig. 2

DEVICE FOR TRANSCATHETER INSERTION INTO THE AORTIC ROOT AT THE SINOTUBULAR JUNCTION

CROSS REFERENCE TO RELATED APPLICATIONS

The present application is a U.S. national stage application of PCT/FR2015/051488 filed on Jun. 4, 2015 designating the United States, and claims foreign priority to French patent application FR 1455144 filed on Jun. 5, 2014, the contents of both documents being herewith incorporated by reference in their entirety.

The invention relates to the technical field of interventional cardiology and of endovascular and minimally invasive surgery and more particularly to an introducer device for intervention by a transcatheter approach.

The invention has an advantageous application, which must not however be considered as limiting, for any type of surgical intervention, for example for replacement of a valve or for valve implantation by a transcatheter approach, more generally known to a person skilled in the art by the acronym TAVI.

Any intervention performed by a transcatheter approach requires the operating surgeon to take very great care since, in a cardiac intervention for example, the blood circulation is not diverted, which is not the case, for example, in open-heart surgery, where there is an extracorporeal circulation of the blood.

The generation of debris from the aortic valve during the TAVI procedure may cause a post-operative coronary embolism, which leads to an infarction after the procedure, while a cerebral embolism may cause iatrogenic stroke.

It is also known that the implantation of an aortic valve by TAVI through a highly calcified native aortic valve often causes paravalvular leaks, which may endanger the patient's life in the medium term. This latter phenomenon is due to the irregularity of the calcifications, which produce imperfect adherence of the TAVI bioprostehsis with the aortic ring of the patient.

In order to obtain better results with TAVI, it appeared important to place the valve on a surface that is as regular as possible in order to avoid a distortion susceptible of rendering the opening of the prosthesis incomplete and, similarly, to improve the contact between the native aortic ring and the bioprostehsis. This has the aim of minimizing the paravalvular leaks which affect the TAVI and which impact on the medium-term survival of the patients.

Proceeding from this prior art, and in order to obtain, for example, a remodeling of the implantation site ranging from medium transcatheter decalcification to complete removal of the native valve leaflets, and with the objective of allowing various procedures and interventions to be performed in complete safety by a transcatheter approach, it appeared important to be able to temporarily fit a device suitable for replacing the function of the native valve. One of the main problems arising in transcatheter decalcification of the aortic valve, with the heart beating and with no extracorporeal circulation, is that of avoiding migration of the calcium debris into the aortic root and downstream into the aortic arch. There is no doubt that this phenomenon is more evident in a transcatheter decalcification procedure than during a standard TAVI procedure, which is presently performed without the decalcification of the aortic valve.

To solve this problem and achieve these objectives, a device has been conceived and developed that is introduced by a transcatheter approach into the aortic root at the sinotubular junction by means of a guide wire and a catheter, with means for protecting the surrounding tissues during placement of said catheter.

According to the invention, the device comprises an assembly serving as a valvular embolic filter, mounted with the ability to slide in a guided manner inside said catheter, said assembly having arrangements capable of forming, in the aortic root, a safety chamber performing a valve function and a protective function against embolic accidents.

As a result of these features, the device makes it possible to perform various interventions by a transcatheter approach, for example removing the calcified tissue and vegetation from within and above the flaps of the aortic valve, fitting any given type of valve in place, etc., the intervention being carried out under the conditions of a physiological circulation and not using an extracorporeal circulation.

To solve the problem of creating this safety chamber, the arrangements of the assembly serving as a valvular embolic filter comprise a tubular body secured, at one of its ends, to a part capable, as and when required, of being either deployed outside the catheter or retracted inside the catheter, said part having filtration arrangements combined with means capable of reproducing a temporary valve function corresponding to opening during the systolic phase and to closing during the diastolic phase, in order to prevent any regurgitation of blood in a deployed position of said part for covering the native aortic valve with a seat secured in the aortic root at the sinuses of Valsalva without obstructing the blood flow.

To solve the problem of reproducing the commissures of the native valve, the part of the embolic filter is in the general shape of a cone and has angularly offset shells, of which the contours envelop the commissures of the native valve, said shells being mounted in combination with a filtering membrane.

As a result of these arrangements, the cone is able to position itself on the floor of the aortic root, in contact with the edge of the aortic ring, and is able to move while remaining below the coronary ostia and at the same time go round the commissures of the native valve.

The positioning of the valvular embolic filter on the aortic root in the area of the commissures is very important for avoiding acute aortic insufficiency during the transcatheter decalcification intervention.

In one embodiment of the active part of the valvular embolic filter, the filtering membrane comprises, on the one hand, a lower layer composed of a mesh network with a porosity suitable for blocking tissue debris while allowing the passage of the blood flow and, on the other hand, an upper layer made of a soft and extensible polymer material for acting as a temporary valve, by simple deformation determined by the systolic pressure.

The layers are fixed together by welding at the base of the cone shape and on the perimeter thereof, said welding being soft and spongy in order to provide an optimal seat of the valve filter on the base of the aortic root.

The meshed lower layer is fixed to the end of the body and in a continuation of the latter, while the upper layer serving as a valve is free and remains open at the top of the cone shape.

According to another feature, the catheter has a radiopaque end capable of protecting the surrounding tissues during introduction and navigation through the aorta. This end is retractable inside the tubular body of the assembly serving as embolic filter. The end is advantageously an inflatable balloon filled with a sterile radiopaque solution.

The invention is explained in more detail below with reference to the figures of the attached drawings, in which:

FIG. 1 is a partial and perspective view showing in particular the assembly serving as a valvular embolic filter, FIG. 2 is a view corresponding to FIG. 1 in partial cross section, FIGS. 3 to 20 show the main steps of a transcatheter intervention using the device according to the invention, in an application to an aortic valve, which application must not be regarded as strictly limiting the invention.

The device according to the invention comprises an assembly (E) serving as a valvular embolic filter, mounted with the ability to slide in a guided manner inside a catheter (1). As will be indicated in the description below, the catheter (1) is equipped with the assembly (E) introduced into the aortic root (RA) by means of a guide wire (g), as is the current practice for this type of intervention.

The filtering assembly (E) has arrangements capable of producing, in the aortic root (RA), a safety chamber performing a valve function and a protective function against embolic accidents. This assembly (E) comprises a body (2) mounted so as to slide freely inside the catheter (1). Of course, the catheter (1) and the body (2) are made of a soft material.

The tubular body (2) is secured, at one of its ends, to a part (2a) which is in the general shape of a cone and is capable of producing the safety chamber as such. This part (2a) is capable, as and when required, of either being deployed outside the catheter (1) or retracted inside the catheter (1). This part (2a) has filtration arrangements combined with means capable of reproducing the temporary valve function corresponding to opening during the systolic phase and to closing during the diastolic phase.

The aim sought is therefore to to prevent any regurgitation of blood in a deployed position of this part (2a) which constitutes the safety chamber, the objective being to cover the native aortic valve with a seat secured in the aortic root and, more precisely, at the junction between the ring and the origin of the sinuses of Valsalva without obstructing the blood flow.

As the figures of the drawings show, in particular FIGS. 1 and 2, the part (2a) of the embolic filter is in the general shape of a cone and has angularly offset shells (3). For example, these shells are offset by 120° in order to reproduce the position of the commissures of the native valve. The base of the conical part formed by the shells (3) is able, for example, to position itself on the floor of the aortic root, to move under the coronary ostium and, at the same time, go round the three commissures of the native valve. It will be noted that, in the case of a bicuspid aortic valve, the conical general shape may be adapted and have only two shells.

These features permit correct positioning of the valvular embolic filter, which is important.

The shells (3) are mounted in combination with a filtering membrane (4). This filtering membrane (4) comprises a layer (4a) designated as lower layer, composed of a mesh network with a porosity suitable for blocking any tissue debris while allowing the passage of the blood flow. Moreover, this filtering membrane (4) has another layer (4b), designated as upper layer, made of a soft and extensible thin polymer material in order to act as a temporary valve, by simple deformation.

The layers (4a), (4b) are fixed together at the base of the conical part formed by the shells (3). Advantageously, this fixing is done by welding (5) on the perimeter of the base of the conical part (2a). The weld is soft and spongy in order to provide an optimal seat for the valvular filter at the base of the aortic root.

The meshed lower layer (4a) is fixed to the end of the body (2) and in a continuation thereof by any known and suitable means. For example, this fixing can likewise be done by welding. Consequently, the upper layer (4b) serving as valve is free and remains open at the top of the conical shape.

The catheter (1) has a radiopaque end able to protect the surrounding tissue during its introduction and its navigation in the aorta. As will be indicated in the description below, the end is retractable inside the assembly serving as embolic filter and, consequently, retractable inside the body (2) of the latter and the catheter (1). Advantageously, this end is formed by an inflatable balloon (6) filled with a sterile radiopaque solution.

Reference is made to FIGS. 3 to 20 showing the different sequences for placement of an aortic valve, noting that the device can be used for other cardiac valves such as tricuspid valves, mitral valves and pulmonary valves, but also for the introduction of instruments such as a decalcifying instrument in order to achieve a remodeling of the implantation site.

Figure 4:
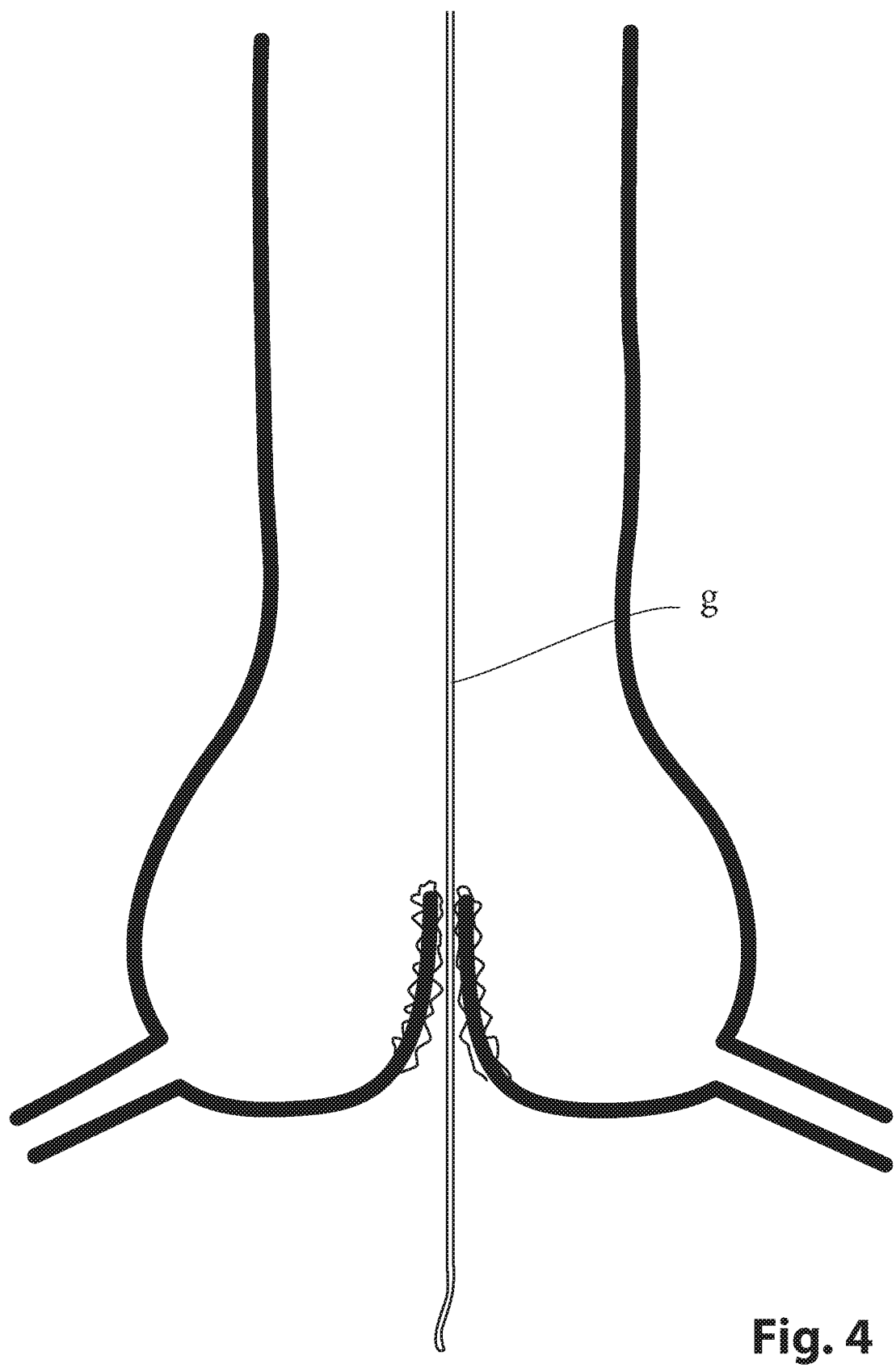

FIG. 3 shows the aortic root, while FIG. 4 shows the same root after placement of the guide wire (g) which is engaged, in a known manner, to pass through the stenosed aortic valve.

Figure 5:
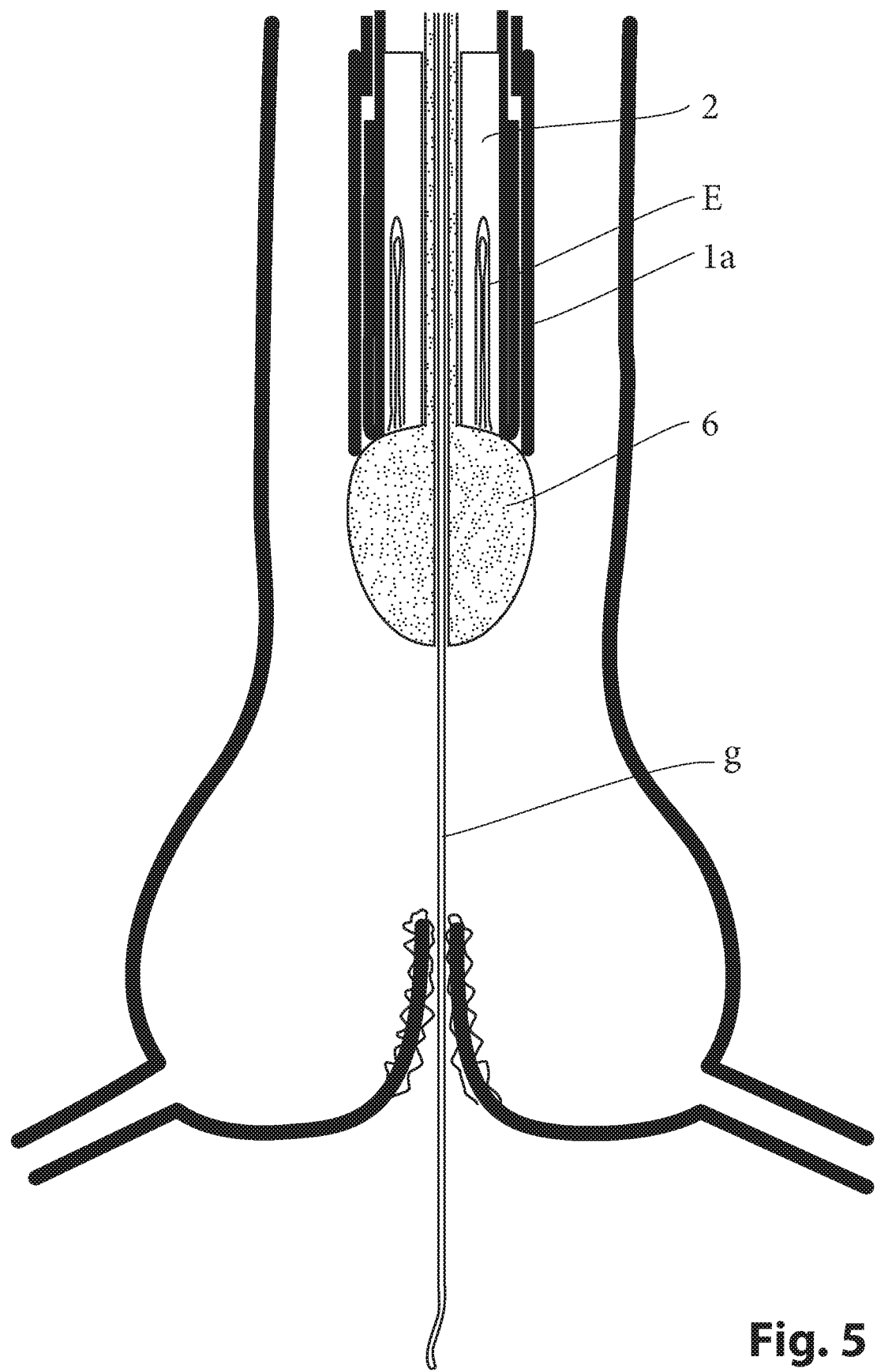

The whole of the introducer device, including the catheter (1) equipped with the assembly (E) serving as valvular embolic filter and the balloon (6), is introduced into the descending aorta by means of the guide wire (g) (FIG. 5). It will be noted that the whole of the device can be introduced directly into the aortic root with a direct juncture of the ascending aorta following trans-aortic access through a small thoracotomy or by means of an endoscopy trocar or alternatively by a transcatheter approach via the femoral artery or via peripheral access such as the subclavian arteries or auxiliary arteries.

Figure 6:
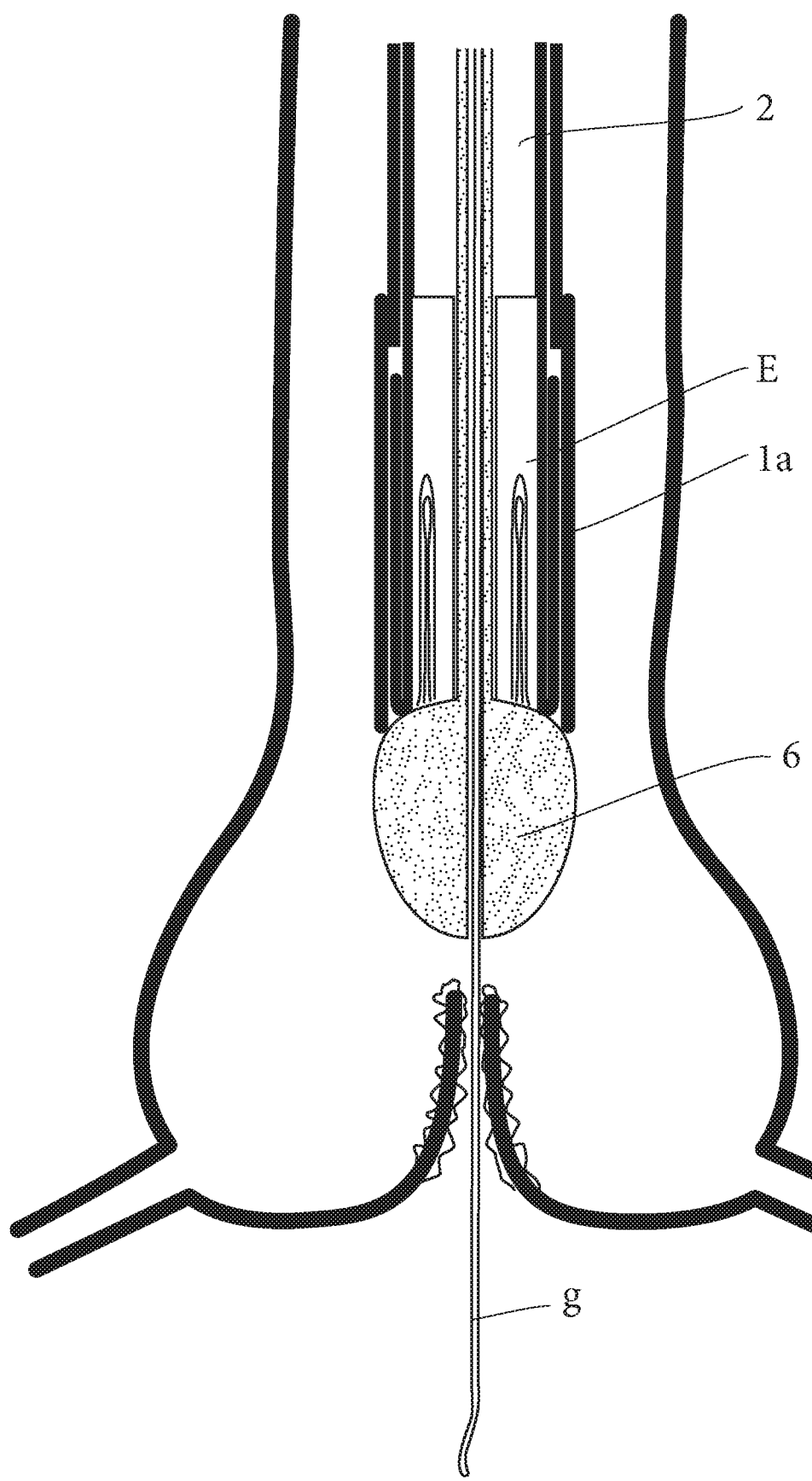
Figure 7:
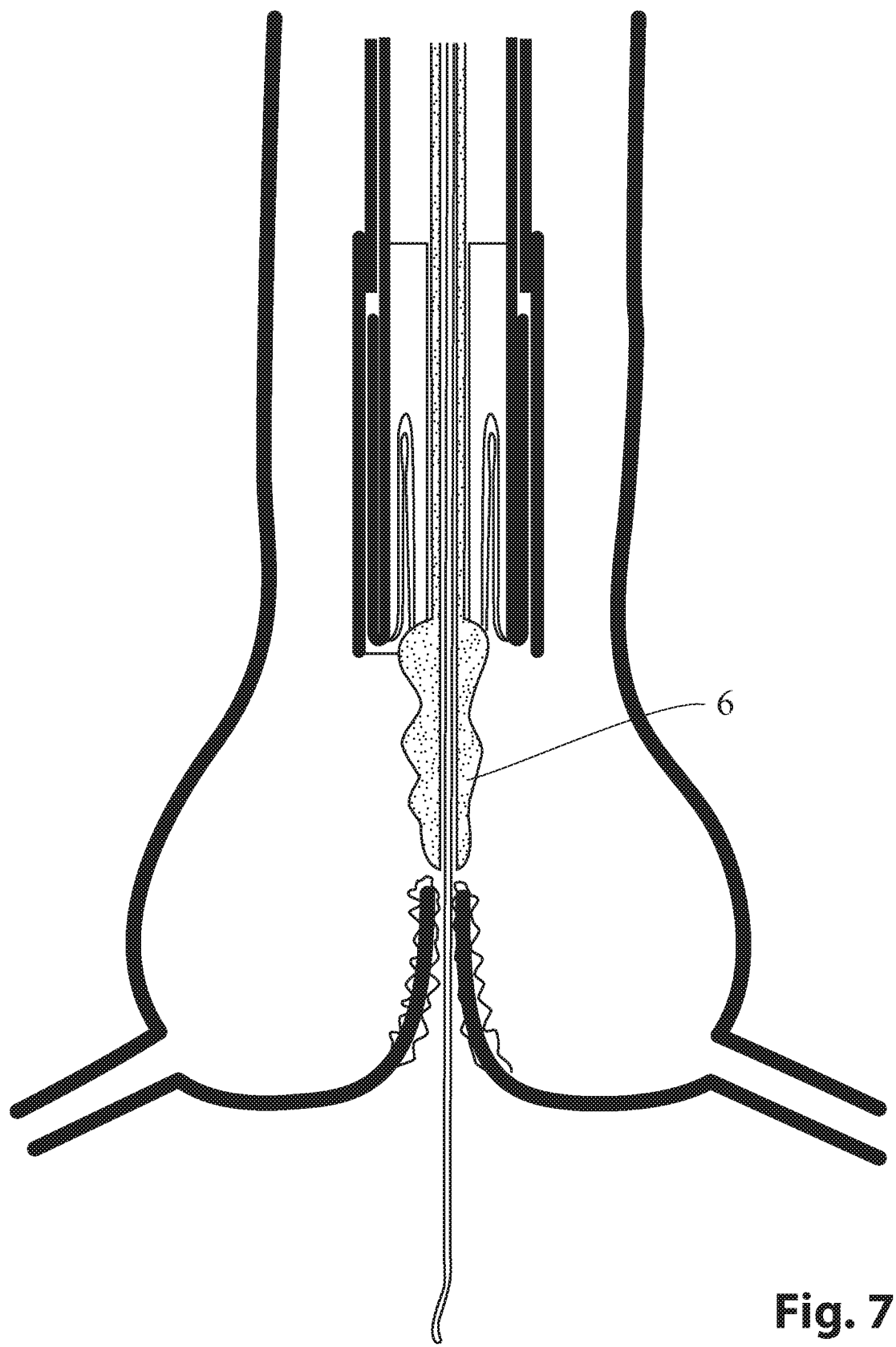
Figure 8:
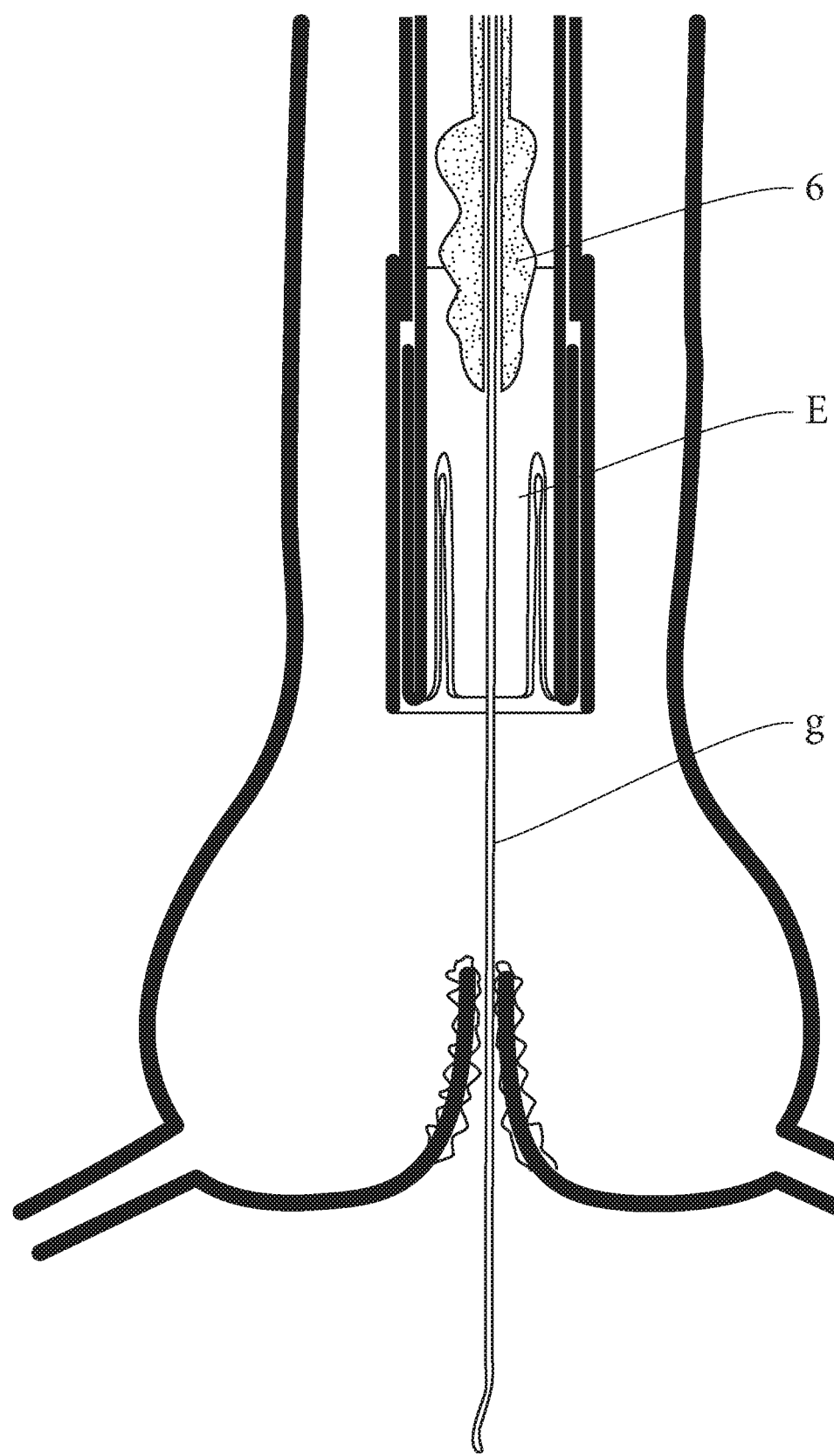

The whole of the introducer catheter is positioned at the sinotubular junction (FIG. 6). When the device is in position, the end of the balloon is deflated (FIG. 7), in such a way that its diameter is smaller than the internal diameter of the introducer device, especially of the tubular body (2) (FIG. 7). The balloon (6) is then completely withdrawn from the device (FIG. 8).

Figure 9:
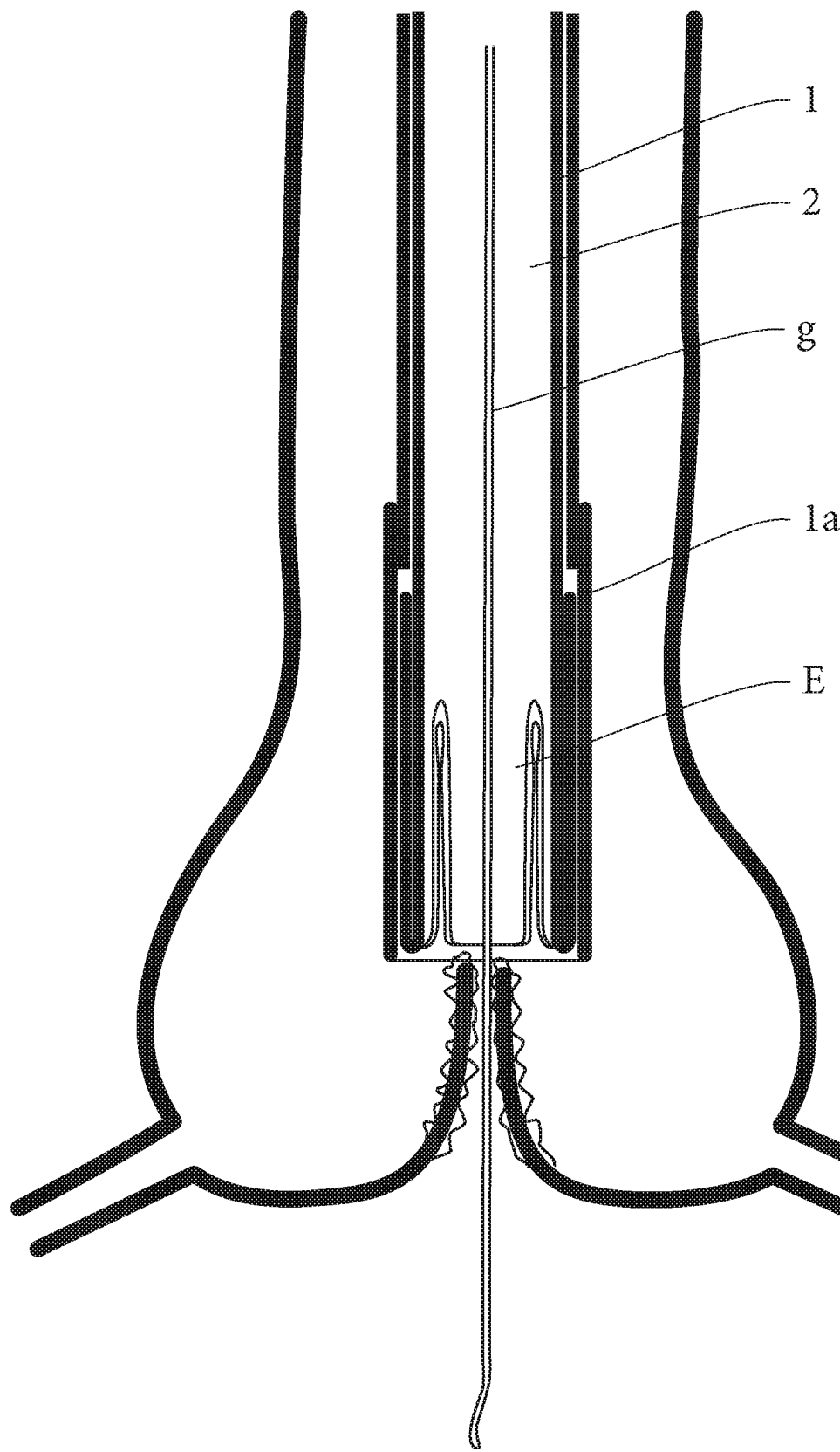

The device is then advanced to the aortic root (FIG. 9).

Figure 10:
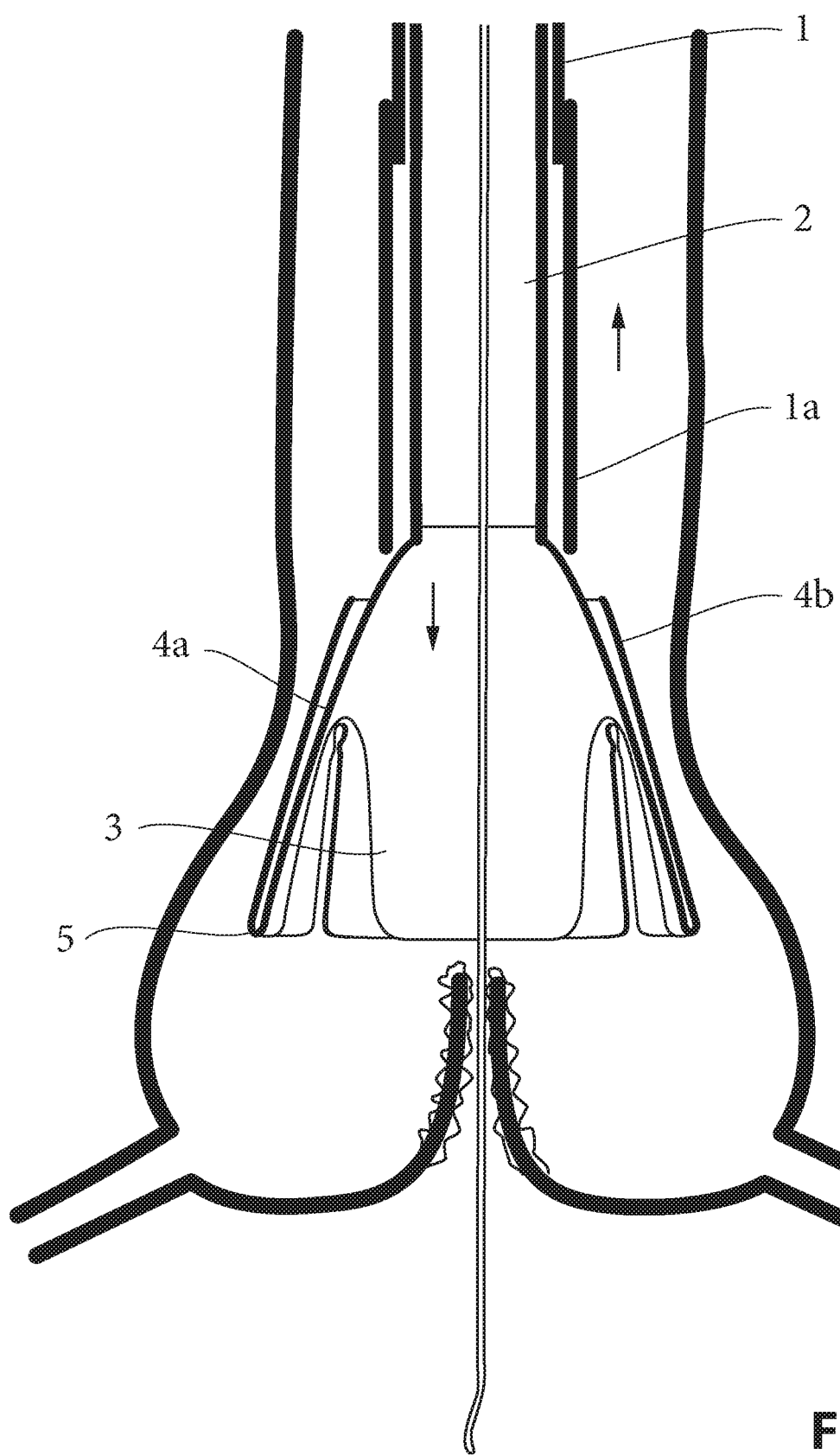
Figure 11:
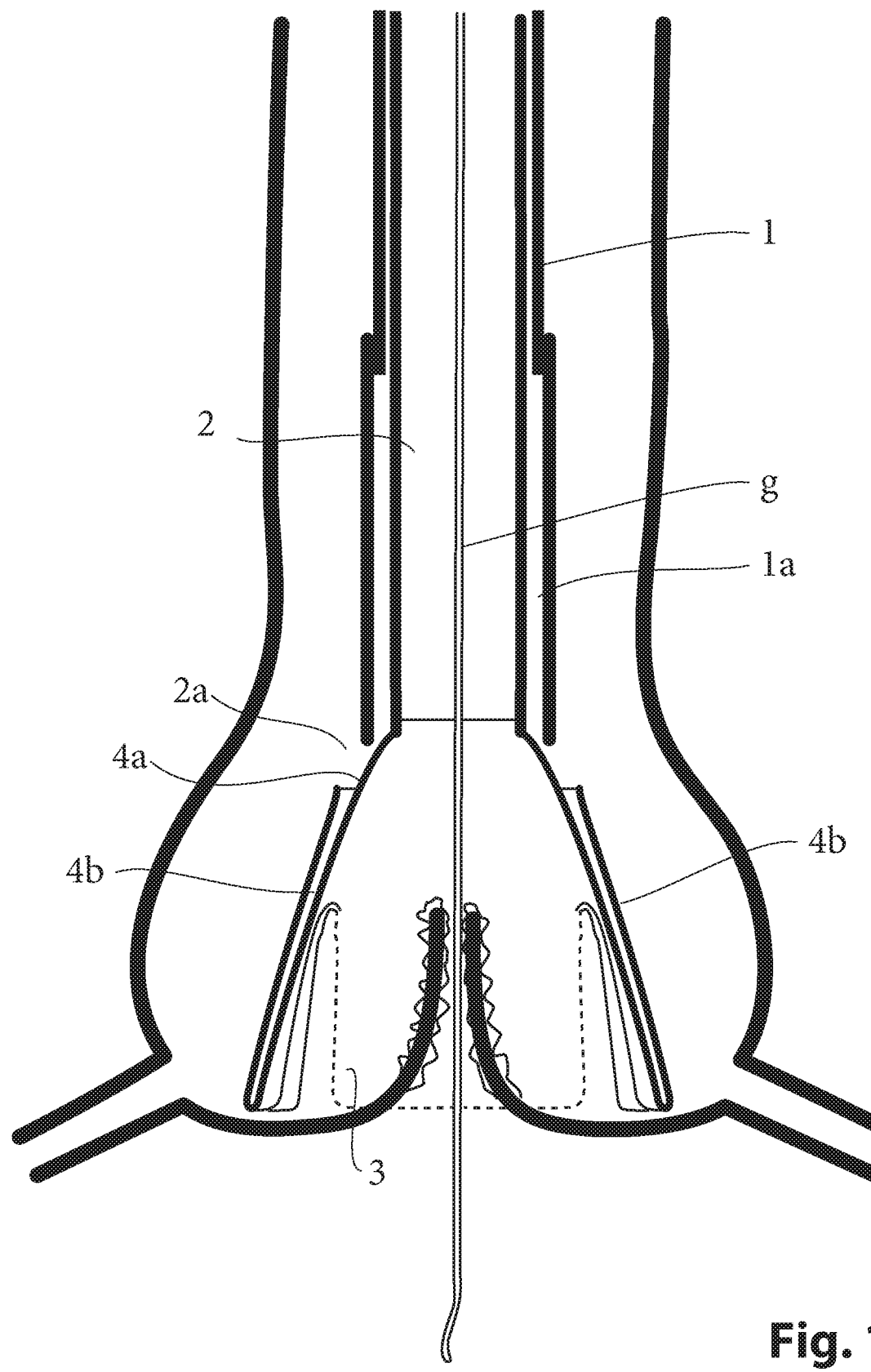
Figure 12:
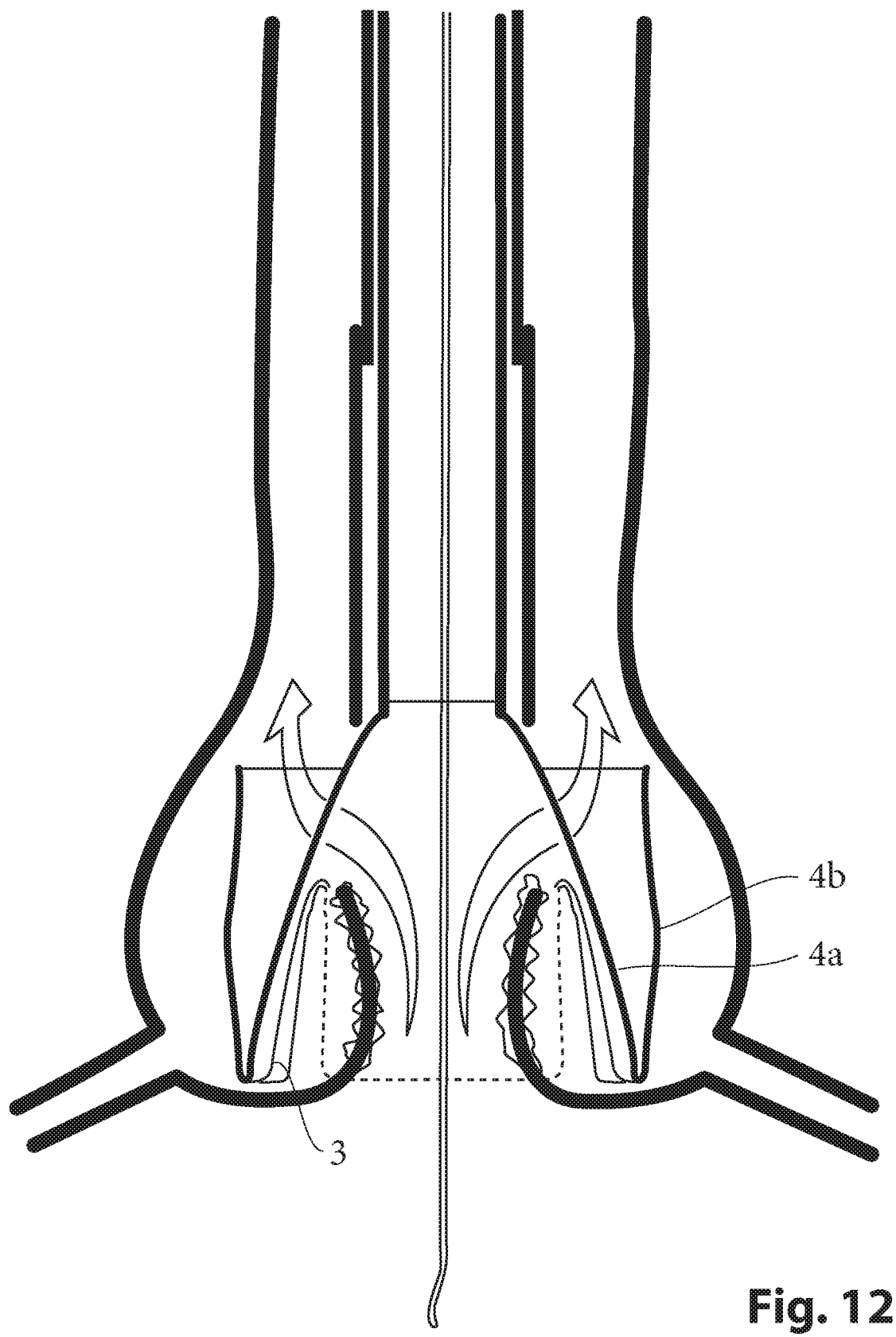

The catheter (1) is then withdrawn (arrow F in FIG. 10), in such a way that the part of the end forming the sheath (1a) covering the assembly (E) of the valvular filter releases the latter, which is partially deployed (FIG. 10). The tubular body (2) is then pushed from the aortic root until the filter assembly, by way of its outer part resulting from the soft weld, comes to bear in the sinuses of Valsalva near the coronary ostium without obstructing the coronary flow (FIG. 11).

The upper layer (4b) of the membrane made of a soft and extensible polymer material acts as a valve ensuring a complete valve function (FIG. 12), while the mesh network of the lower layer (4a) blocks the tissue debris. As indicated, the shells (3) conform to the commissures of the native valve, thereby permitting good sealing and complete seating of the device on the floor of the aortic root.

Figure 13:
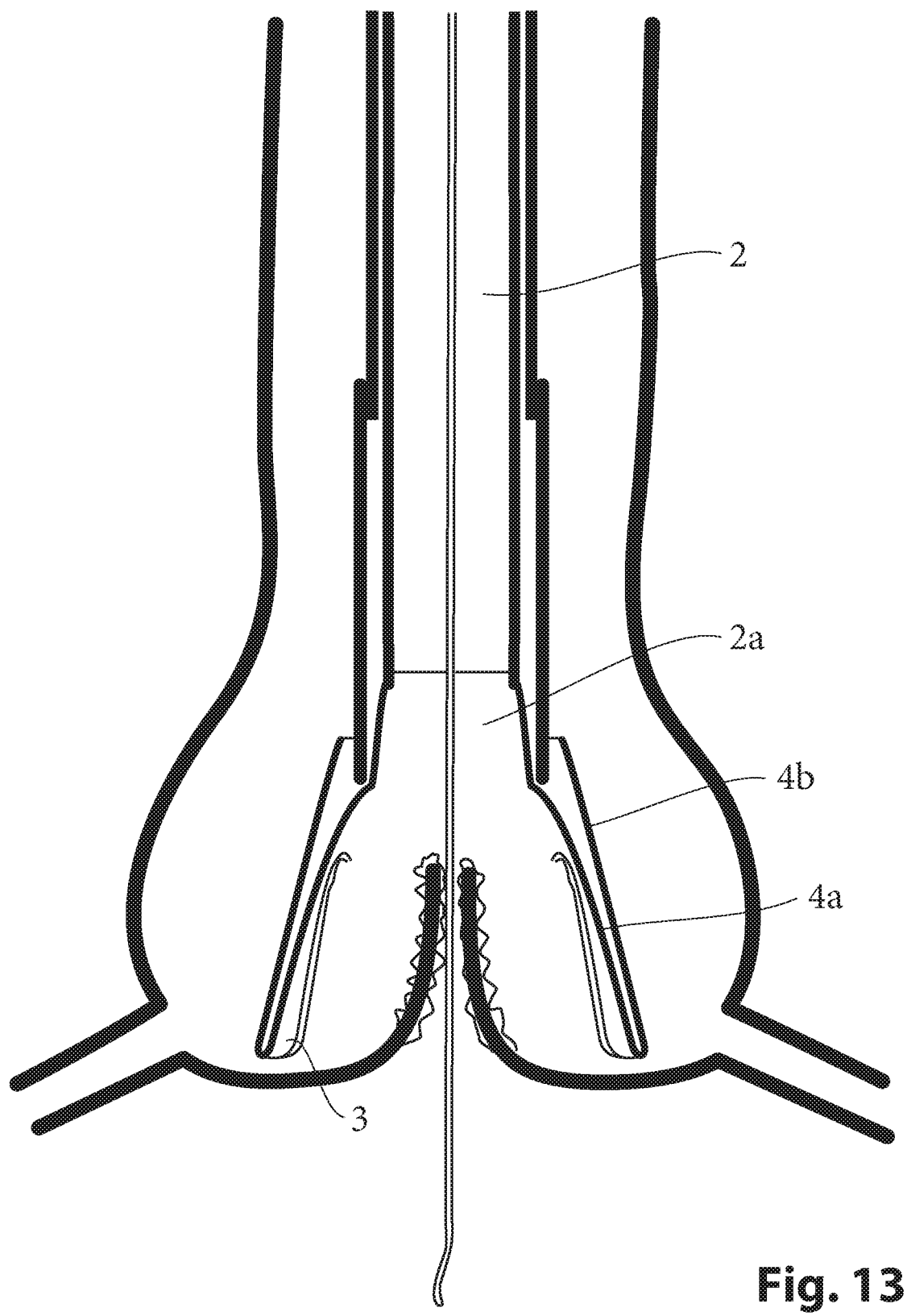

As is shown in FIG. 13, the opening the valvular conical filter can be modified by acting on the catheter (1), of which the end (1a) forms a sheath cooperating with said filter in order to modify the opening of the filter restrictively (FIG. 13).

Figure 14:
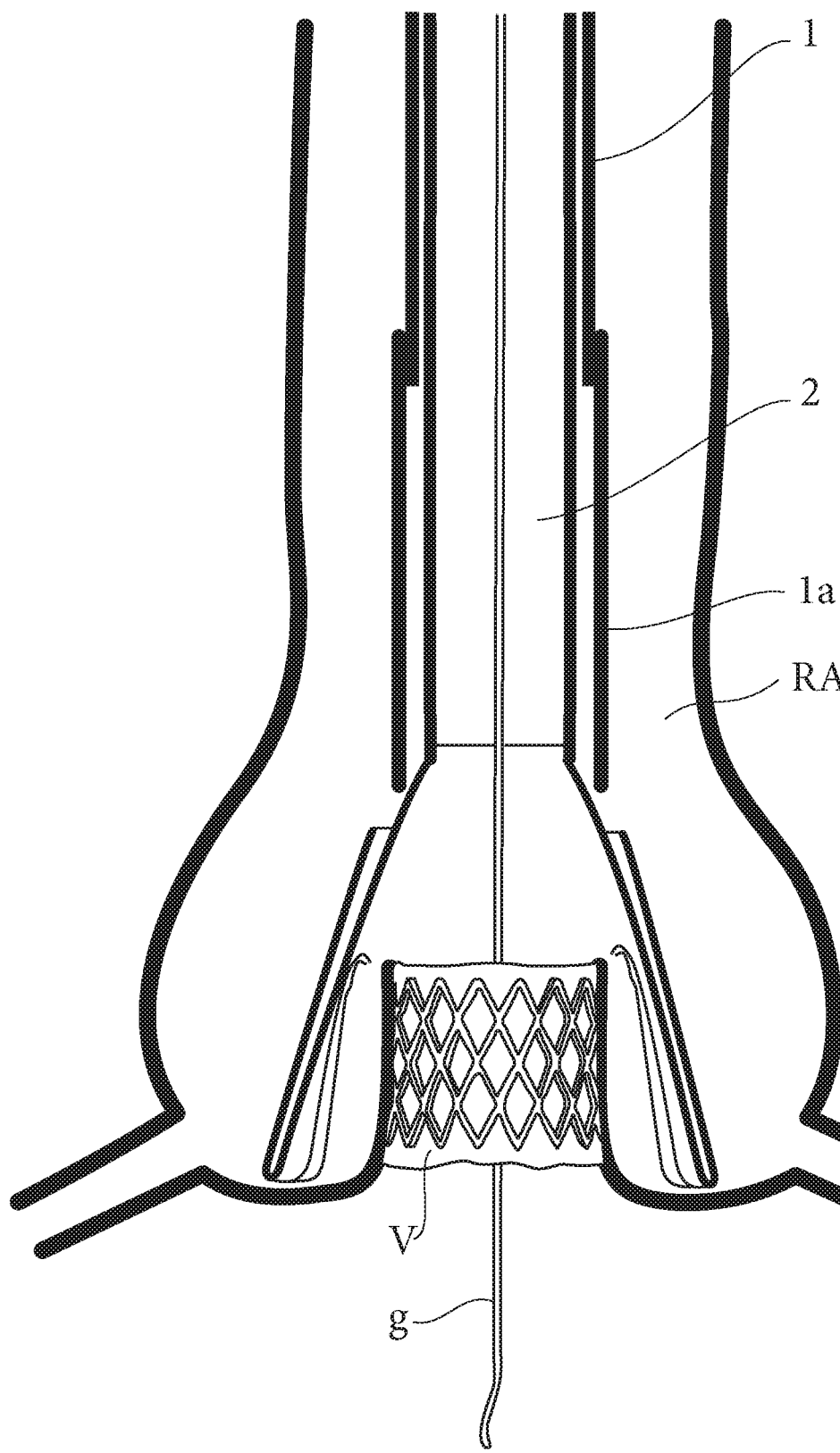
Figure 15:
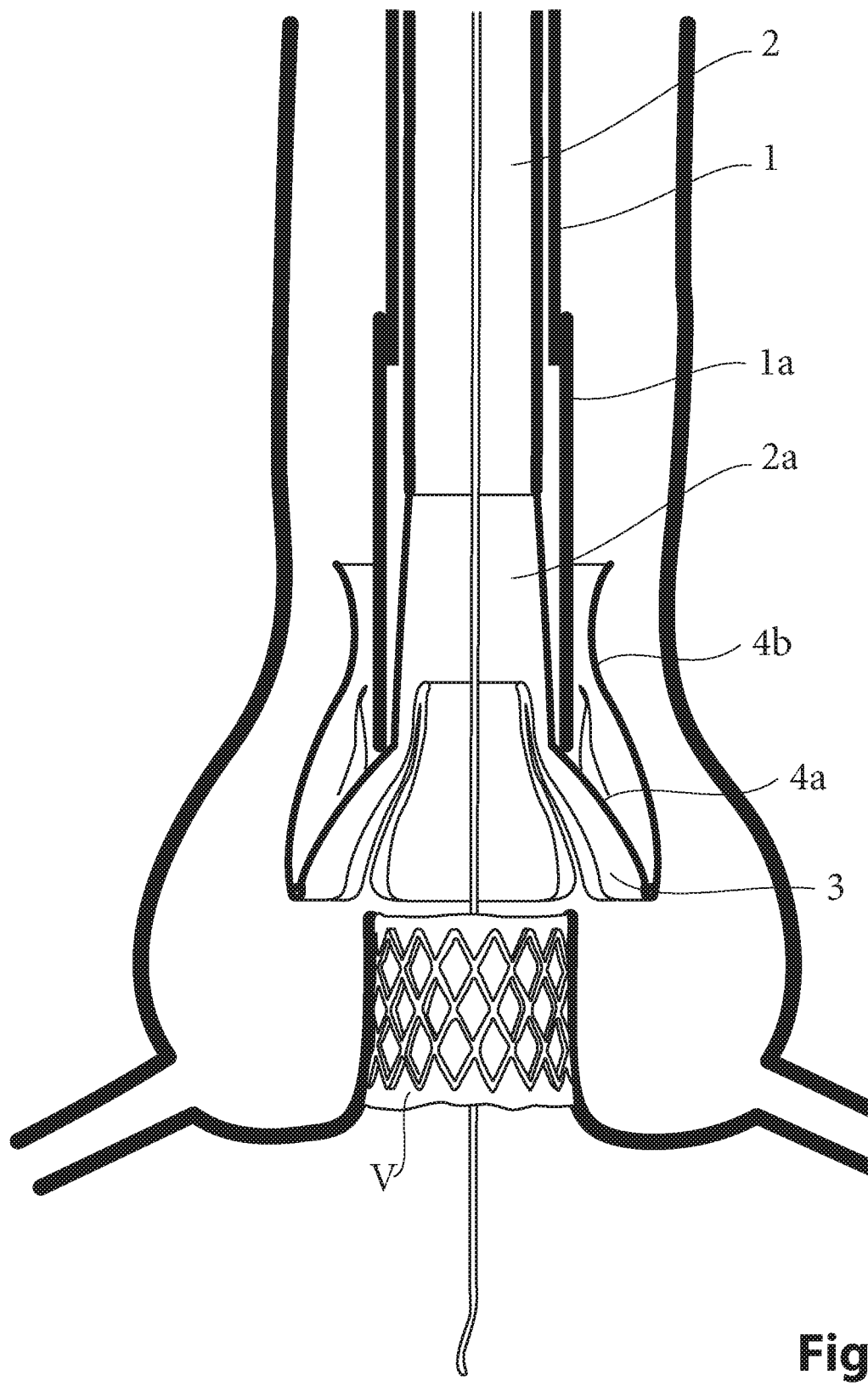
Figure 16:
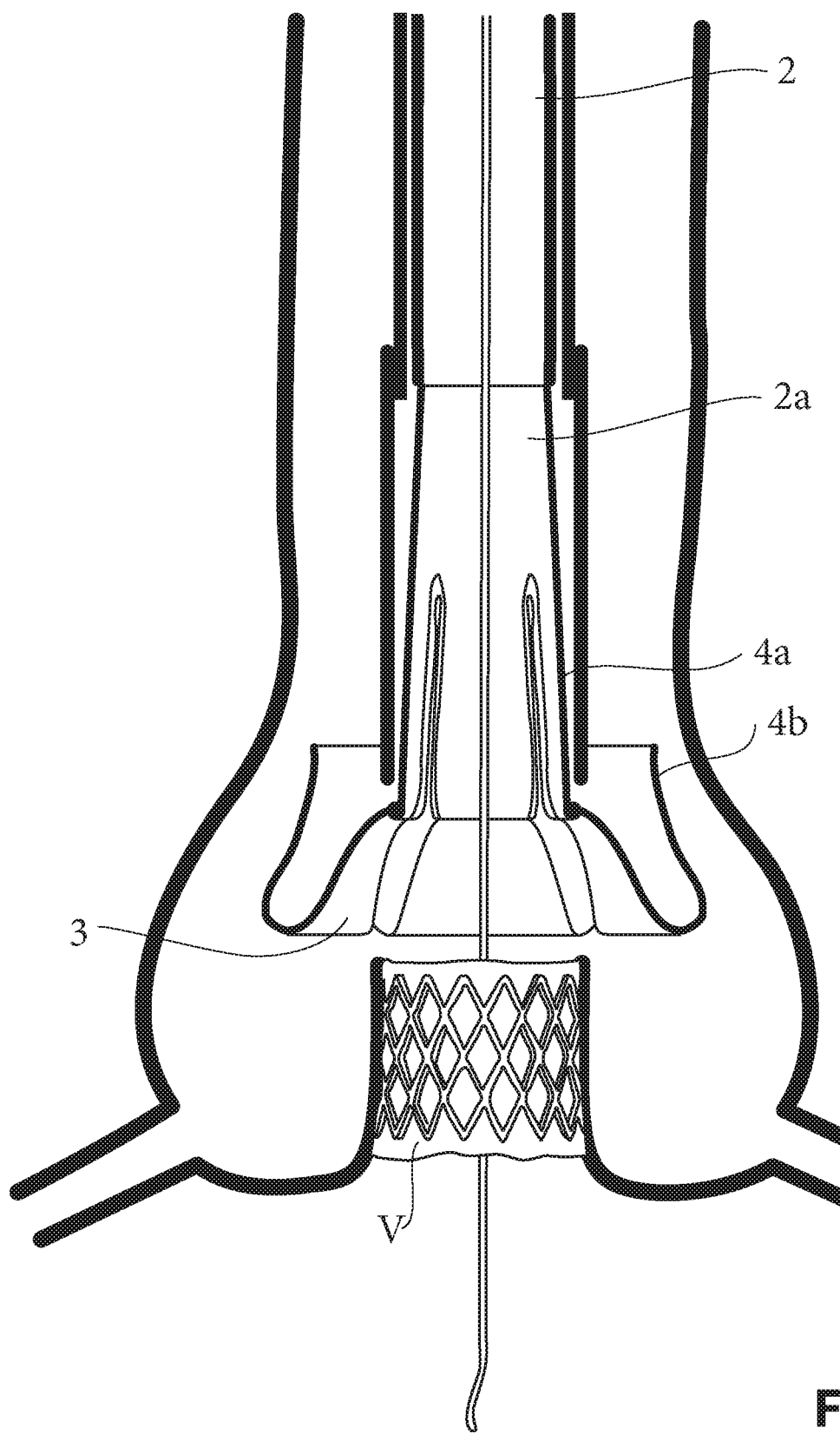
Figure 17:
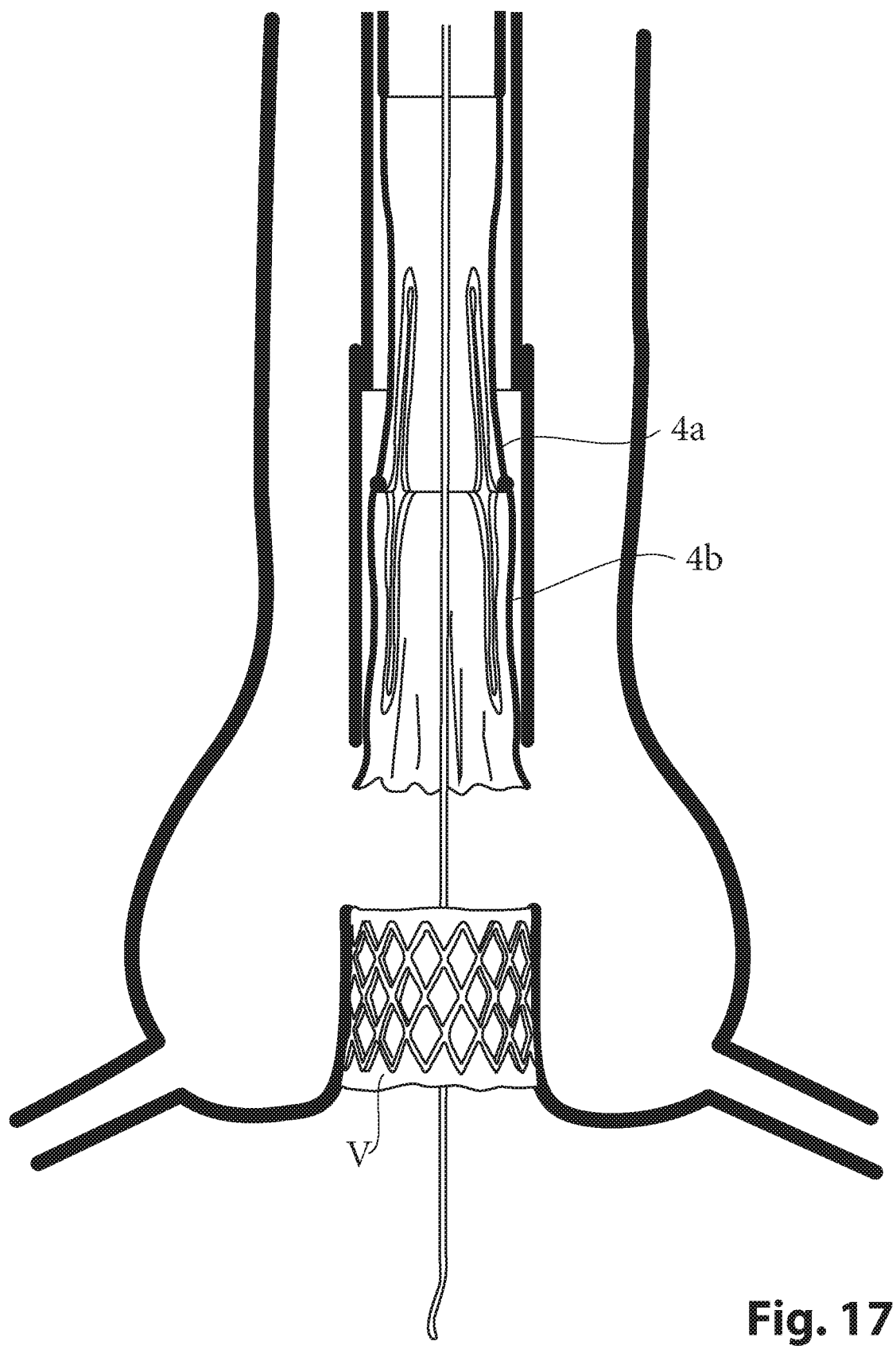
Figure 18:
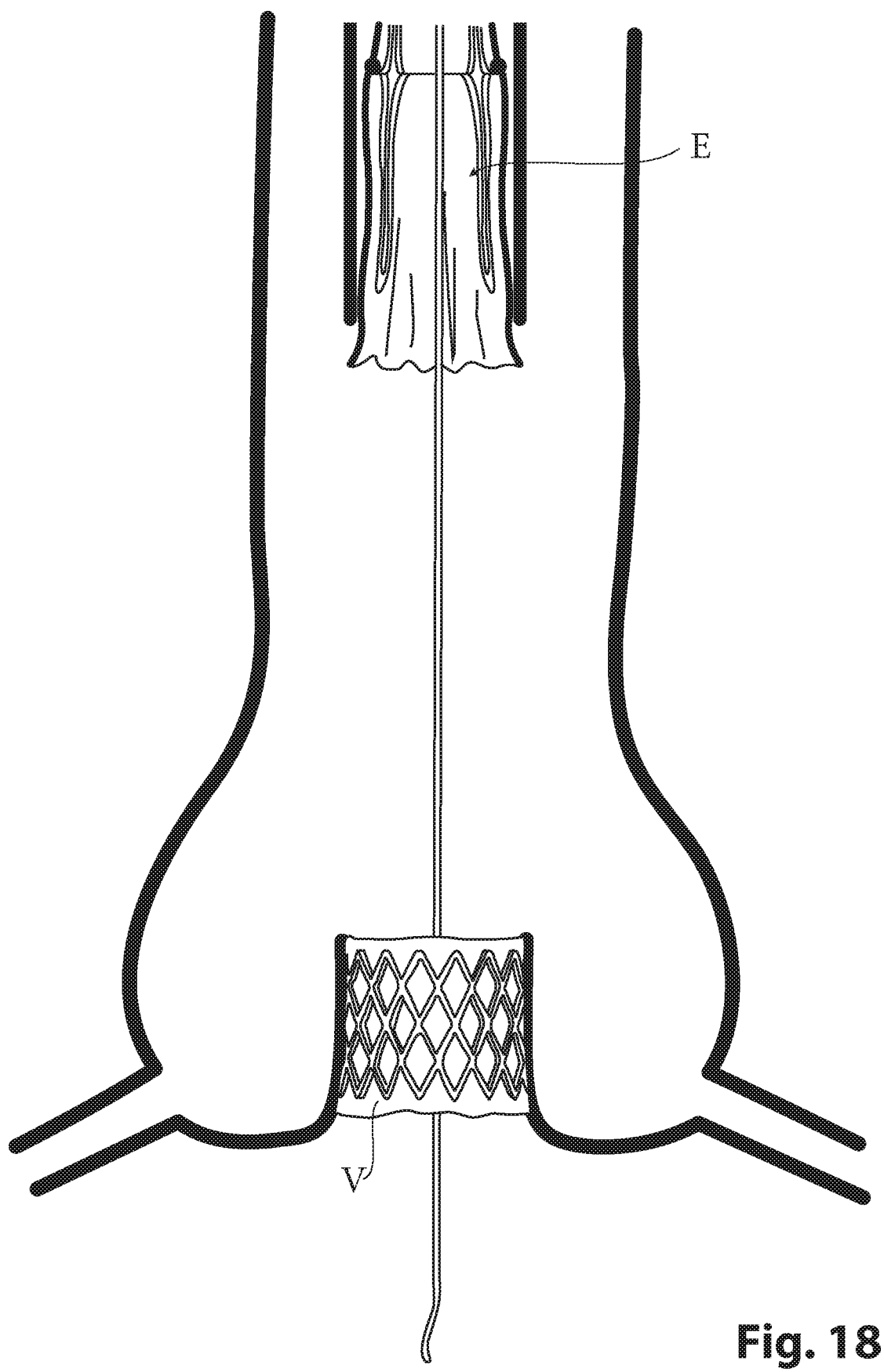

Having verified the stable position of the catheter (1), it is possible, by way of the catheter, to introduce the chosen medical device, for example a valve (V) (FIG. 14). If necessary, prior to the placement of the valve, it is possible to carry out decalcification by any known and suitable means.

It will be noted that if the tissue of the leaflets to be removed has been limited and regurgitation is medium to moderate, the introducer device can be removed and the transcatheter valve can be implanted.

Conversely, if the tissue ablation has been completed with total removal of the flaps, it is important to keep the introducer device in place in order to ensure the temporary valve function to prevent aortic insufficiency, which could pose a threat to the life of the patient during the surgical intervention.

When the valve function of the conical filter is terminated, the device can be withdrawn.

The withdrawal of the device involves the closure of the filter membrane, ensuring that the trapped debris is not embolized. The valvular filter is gently withdrawn from the root of the aortic valve (FIG. 15) and is progressively reintroduced into the catheter. The sheath (1a) of the catheter (1) is slid down between the polymer material of the membrane and the polymer filter (FIGS. 16, 17 and 18) until reaching the end of the conical part, closing it up gradually to tilt the shells (3), which are retracted inside the catheter (1) over the polymer material by sliding in order to clear the debris trapped in the filter.

Figure 19:
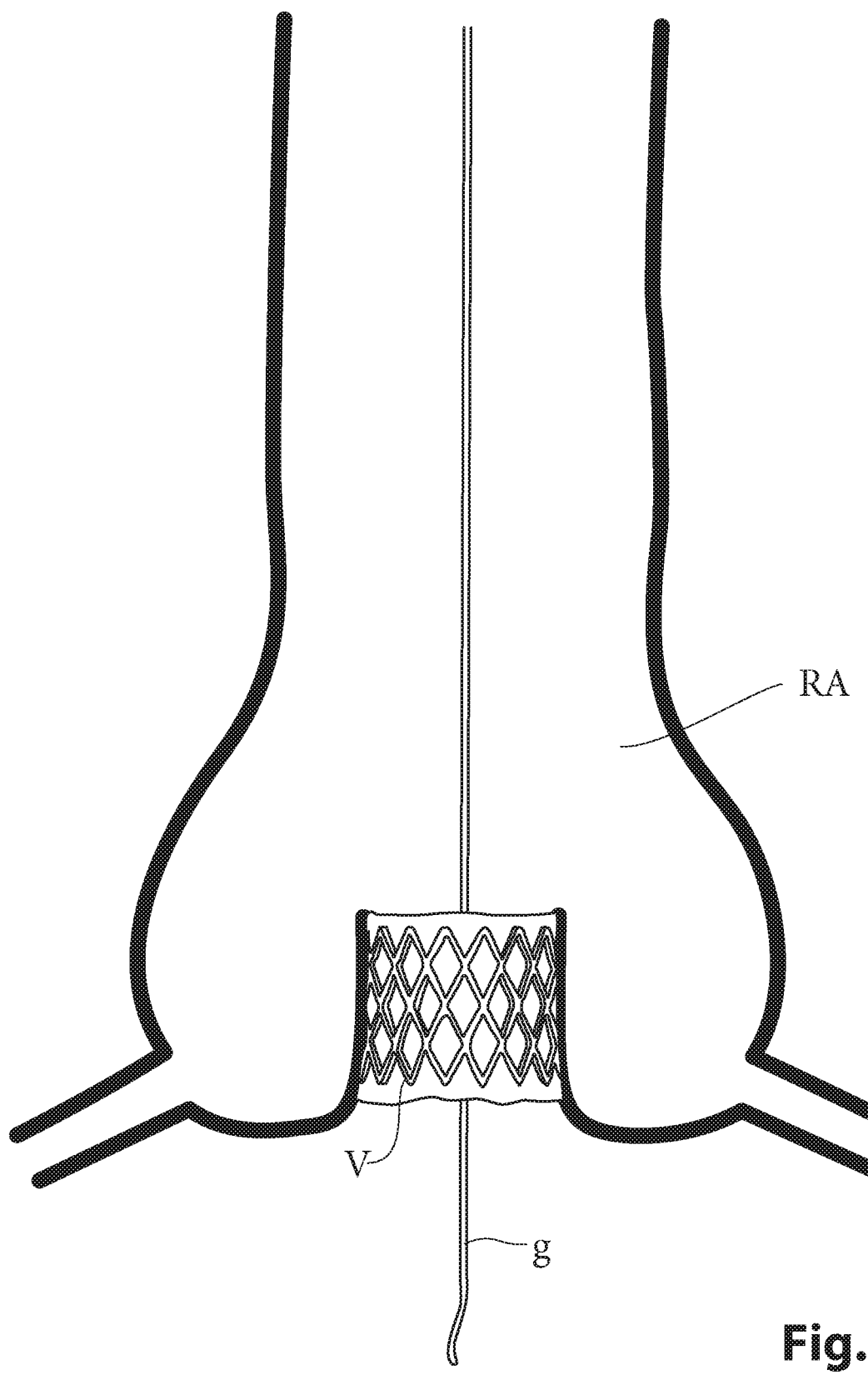
Figure 20:
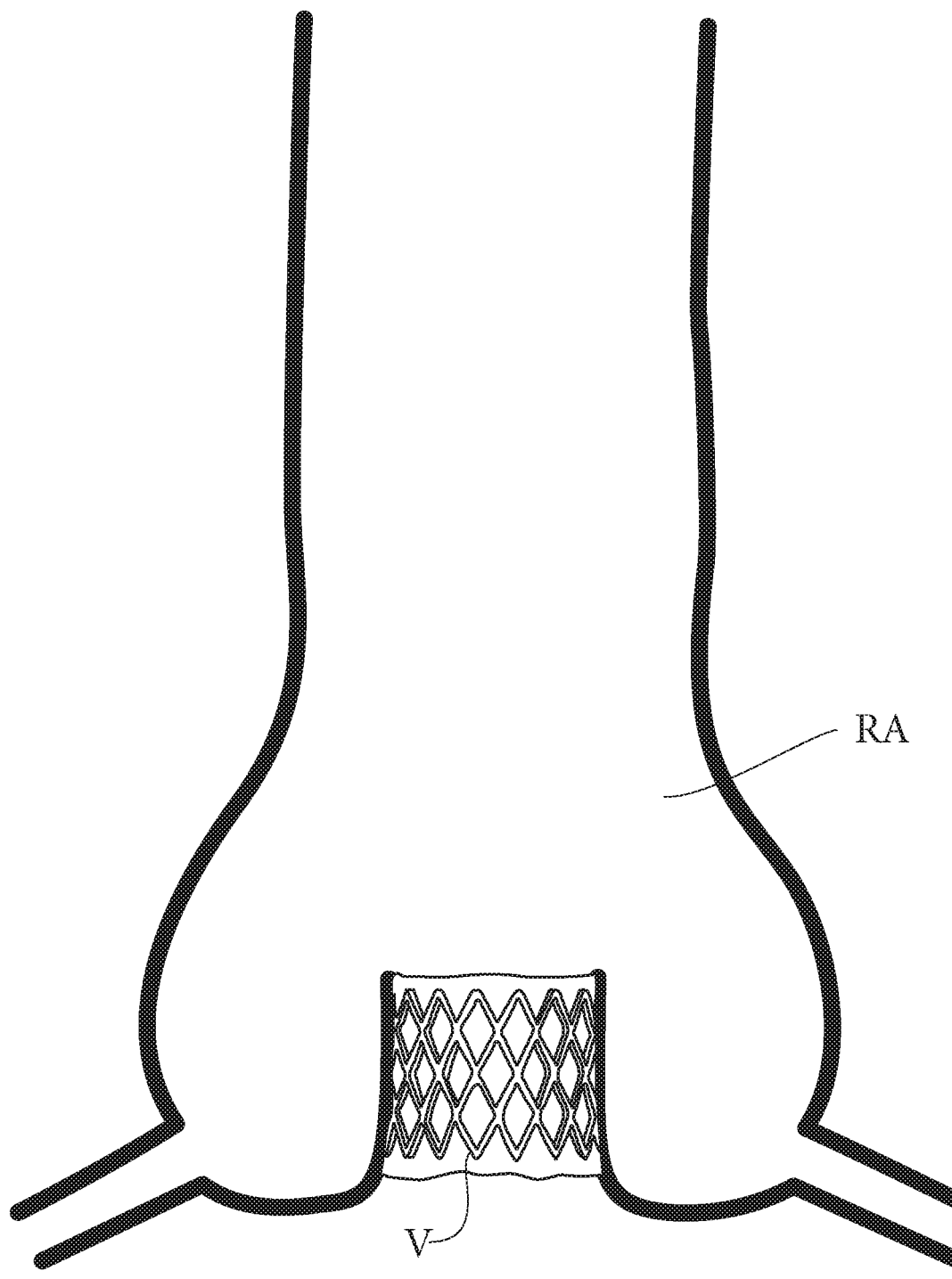

When the withdrawal procedure has been completed and the valvular filter has been fully closed, the device can be withdrawn in complete safety from the aorta (FIG. 19). It is then a simple matter of removing the guide wire (FIG. 20).

The advantages are clear from the description.

The invention claimed is:

1. A device for transcatheter insertion into an aortic root at a sinotubular junction by a guide wire and a catheter for protecting surrounding tissues, comprising:
    an assembly serving as a valvular embolic filter, configured to slide in a guided manner inside the catheter, the assembly configured to form, in the aortic root of an aorta, a safety enclosure ensuring a valve function and a protective function against embolic accidents,
    wherein the assembly includes,
    a tubular body; and
    a filtration and valve part configured to deploy outside the catheter or retract inside the catheter,
    wherein the tubular body is secured, at one end, to the filtration and valve part,
    wherein the filtration and valve part is deformable and conical and forms the valvular embolic filter and a temporary valve, the temporary valve configured to open during a systolic phase and to close during a diastolic phase,
    wherein the filtration and valve part is configured to prevent regurgitation of blood when deployed outside the catheter for covering a native aortic valve with a seat secured in the aortic root at sinuses of valsalva without obstructing a blood flow, and
    wherein the filtration and valve part includes a plurality of angularly offset shells opening towards the aortic root and a filtering membrane, the filtering membrane including a first layer made of a mesh network having a porosity for blocking tissue debris while allowing a passage of blood, and a second layer configured to form a valve by deformation, the first layer and the second layer are fixed together at a base of the conical filtration and valve part.

2. The device as claimed in claim 1, wherein contours of the angularly offset shells of the filtration and valve part are circumventing commissures of the native aortic valve, the angularly offset shells mounted together with the filtering membrane.

3. The device as claimed in claim 2, wherein the second layer of the filtering membrane includes a soft and extensible polymer material for acting as the temporary valve by the deformation.

4. The device as claimed in claim 3, wherein
    the first layer and the second layer are fixed together by a weld at the base of the conical filtration and valve part,
    the weld being soft and spongy at a perimeter to provide a seat for the filtration and valve part on a base of the aortic root and to allow an end of the conical shape to close progressively, until retraction inside the catheter, by virtue of the polymer material, by sliding the catheter downwardly between the first layer and the second layer of the filtering membrane until reaching the end of the conical shape to clear the tissue debris.

5. The device as claimed in claim 3, wherein the first layer is fixed to the one end of the tubular body and in a continuation of the tubular body, and the second layer is free and remains open at a top of the conical shape.

6. A system for transcatheter insertion into an aortic root at a sinotubular junction by a guide wire for protecting surrounding tissues, comprising:
    a catheter; and
    an assembly serving as a valvular embolic filter, configured to slide in a guided manner inside the catheter, the assembly configured to form, in the aortic root of an aorta, a safety enclosure ensuring a valve function and a protective function against embolic accidents,
    wherein the assembly includes,
    a tubular body; and
    a filtration and valve part configured to deploy outside the catheter or retract inside the catheter,
    wherein the tubular body is secured, at one end, to the filtration and valve part,
    wherein the filtration and valve part and forms the valvular embolic filter and a temporary valve, the temporary valve configured to open during a systolic phase and to close during a diastolic phase,
    wherein the filtration and valve part is configured to prevent regurgitation of blood when deployed outside the catheter for covering a native aortic valve with a seat secured in the aortic root at sinuses of valsalva without obstructing a blood flow,
    wherein the catheter and an end of the catheter are configured to slide to modify an opening of the valvular embolic filter, and
    wherein the filtration and valve part is deformable and conical and includes a plurality of angularly offset shells opening towards the aortic root and a filtering membrane, the filtering membrane including a first layer made of a mesh network having a porosity for blocking tissue debris while allowing a passage of blood, and a second layer configured to form a valve by deformation, the first layer and the second layer are fixed together at a base of the conical filtration and valve part.

7. The device as claimed in claim 6, wherein the catheter has a radiopaque end configured to protect the surrounding tissues during and introduction and navigation through the aorta.

8. The device as claimed in claim 7, wherein the radiopaque end is retractable inside the tubular body of the assembly serving as the valvular embolic filter.

9. The device as claimed in claim 7, wherein the radiopaque end includes an inflatable balloon filled with sterile radiopaque solution.

10. A device for transcatheter insertion into an aortic root at a sinotubular junction by a guide wire for protecting surrounding tissues, comprising:
   a valvular embolic filter means for sliding in a guided manner inside a catheter, the valvular embolic filter means forming, in the aortic root of an aorta, a safety enclosure ensuring a valve function and a protective function against embolic accidents,
   wherein the valvular embolic filter means includes,
   a tubular body; and
   a filtration means for deploying outside the catheter or retract inside the catheter,
   wherein the tubular body is secured, at one end, to the filtration means,
   wherein the filtration means is deformable and conical and includes a filter and a temporary valve, the temporary valve configured to open during a systolic phase and to close during a diastolic phase,
   wherein the filtration means prevents regurgitation of blood when deployed outside the catheter for covering a native aortic valve with a seat secured in the aortic root at sinuses of valsalva without obstructing blood flow, and
   wherein the filtration means includes a plurality of angularly offset shells opening towards the aortic root and a filtering membrane, the filtering membrane including a first layer made of a mesh network having a porosity for blocking tissue debris while allowing a passage of blood, and a second layer configured to form a valve by deformation, wherein the first layer and the second layer are fixed together at a base of the conical filtration means.

11. The device as claimed in claim 10, wherein contours of the angularly offset shells of the filtration means are circumventing commissures of the native aortic valve, the angularly offset shells mounted together with the filtering membrane.

12. A system for transcatheter insertion into an aortic root at a sinotubular junction by a guide wire for protecting surrounding tissues, comprising:
   a catheter; and
   an assembly serving as a valvular embolic filter, configured to slide in a guided manner inside the catheter, the assembly configured to form, in the aortic root of an aorta, a safety enclosure ensuring a valve function and a protective function against embolic accidents,
   wherein the assembly includes,
   a tubular body; and
   a filtration and valve part configured to deploy outside the catheter or retract inside the catheter,
   wherein the tubular body is secured, at one end, to the filtration and valve part,
   wherein the filtration and valve part and forms the valvular embolic filter and a temporary valve, the temporary valve configured to open during a systolic phase and to close during a diastolic phase,
   wherein the filtration and valve part is configured to prevent regurgitation of blood when deployed outside the catheter for covering a native aortic valve with a seat secured in the aortic root at sinuses of valsalva without obstructing a blood flow,
   wherein the catheter and an end of the catheter are configured to slide to modify an opening of the valvular embolic filter, and
   wherein the catheter has a radiopaque end configured to protect the surrounding tissues during and introduction and navigation through the aorta, and the radiopaque end is retractable inside the tubular body of the assembly serving as the valvular embolic filter.

* * * * *